United States Patent [19]

Nachbur et al.

[11] 3,994,971
[45] Nov. 30, 1976

[54] PHOSPHORUS-CONTAINING CONDENSATION PRODUCTS

[75] Inventors: Hermann Nachbur, Dornach; Arthur Maeder, Therwil, both of Switzerland

[73] Assignee: Ciba-Geigy Corporation, Ardsley, N.Y.

[22] Filed: Aug. 13, 1975

[21] Appl. No.: 604,411

Related U.S. Application Data

[63] Continuation of Ser. No. 285,269, Aug. 31, 1972, abandoned.

[30] Foreign Application Priority Data

Sept. 10, 1971 Switzerland.................. 13303/71

[52] U.S. Cl. .................. 260/551 C; 106/15 FP; 252/8.1; 260/2 P; 260/551 P; 260/249.6; 427/439; 428/276; 260/309.7
[51] Int. Cl.² .................. C07C 125/08; C07F 9/22; C09K 3/28
[58] Field of Search.................. 260/551 C, 551 P

[56] References Cited

UNITED STATES PATENTS

| 3,878,245 | 4/1975 | Nachbur et al. | 260/553 R |
|---|---|---|---|
| 3,887,553 | 6/1975 | Nachbur et al. | 260/249.6 |
| 3,931,310 | 1/1976 | Nachbur et al. | 260/551 P |

FOREIGN PATENTS OR APPLICATIONS

| 1,294,340 | 5/1969 | Germany |
|---|---|---|
| 761,985 | 11/1956 | United Kingdom |
| 740,269 | 11/1955 | United Kingdom |

OTHER PUBLICATIONS

Normand et al., American Dyestuff Reporter, pp. 46–48, (Sept., 1970).
Daigle et al., CA 81:93000k, (1974).
Daigle et al., CA 81:65145t, (1974).
Imamura et al., CA 80:61020e, (1974).

*Primary Examiner*—Floyd D. Higel
*Assistant Examiner*—Thomas A. Waltz
*Attorney, Agent, or Firm*—Joseph G. Kolodny; Edward McC. Roberts; Parabodh I. Almaula

[57] ABSTRACT

The subject of the invention is a process for the manufacture of water-soluble condensation products of hydroxymethylphosphonium compounds and cyanamide, characterized in that (a) one mol of a tetrakis-(hydroxymethyl)-phosphonium compound is condensed with (b) 0.02 to 0.5 mol, preferably 0.1 to 0.3 mol, of cyanamide at 40° to 120° C, optionally in the presence of formaldehyde or a formaldehyde-donating agent and optionally in the presence of an inert organic solvent, and optionally subsequently further condensed at temperatures of 100° to 150° C and, if appropriate, free hydroxyl groups are at least partially etherified with at least one alkanol with 1 to 4 carbon atoms and if appropriate the salts of the condensation products are converted into the corresponding hydroxides.

9 Claims, No Drawings

PHOSPHORUS-CONTAINING CONDENSATION PRODUCTS

This is a continuation of application Ser. No. 285,269, filed on Aug. 31, 1972.

The condensation products are used for flameproofing organic fibre material, especially textiles.

The subject of the invention is a process for the manufacture of water-soluble condensation products of hydroxymethylphosphonium compounds and cyanamide, characterised in that (a) one mol of a tetrakis-(hydroxymethyl)-phosphonium compound is condensed with (b) 0.02 to 0.5 mol, preferably 0.1 to 0.3 mol, of cyanamide at 40° to 120° C, optionally in the presence of formaldehyde or a formaldehyde-donating agent and optionally in the presence of an inert organic solvent, and optionally subsequently further condensed at temperatures of 100° to 150° C and, if appropriate, free hydroxyl groups are at least partially etherified with at least one alkanol with 1 to 4 carbon atoms and if appropriate the salts of the condensation products are converted into the corresponding hydroxides.

The condensation is preferably carried out at 70° to 110° C in an inert organic solvent or solvent mixture. For this, aromatic hydrocarbons are above all suitable, such as, for example, toluene, o-, m- or p-xylene or a mixture thereof, or xylene-toluene, xylene-benzene or xylene-decahydronaphthalene mixtures. Preferably, the optional subsequent further condensation is carried out at 125° to 140° C or in particular at about 135° C, that is to say at the boiling point of the solvent or the solvent mixture.

At the same time it is however also possible to carry out the condensation in the absence of an inert organic solvent, for example if condensation product already manufactured is used as the solvent or if condensation is carried out in the melt.

An appropriate procedure is to heat the tetrakis-(hydroxymethyl)-phosphonium compound, which as a rule is present as an aqueous solution, to the boil together with the component (b), optionally in a solvent, and to distil off the water. Possible tetrakis-(hydroxymethyl)-phosphonium compounds are above all salts and the hydroxide.

Amongst the tetrakis-(hydroxymethyl)-phosphonium salts used, the halides, such as, for example, the bromide or especially the chloride are preferred. Tetrakis-(hydroxymethyl)-phosphonium chloride is hereafter referred to as THPC.

Where tetrakis-(hydroxymethyl)-phosphonium hydroxide (THPOH) is used as the starting product, it is appropriately prepared beforehand from a corresponding salt, for example THPC, by neutralisation in aqueous solution with a base, for example sodium hydroxide, and subsequent dehydration.

The optionally conjointly used formaldehyde is preferably present as an aqueous solution. Paraformaldehyde can above all be used as a formaldehyde-donating agent.

The etherification of the condensation product still containing free hydroxyl groups, which is optionally to be carried out, is effected, for example, with n-butanol, n-propanol, ethanol or especially methanol. Preferably, it is carried out in an acid medium.

The acid catalysts optionally used conjointly in the condensation are preferably salts which have an acid action (Lewis acids), such as magnesium chloride, iron-III chloride, zinc nitrate or boron trifluoride/diethyl ether. The conjoint use of these catalysts is especially advisable in the condensation of THPOH.

After completion of the condensation and optional etherification, the salts of the condensation products can also be completely or partially converted into their corresponding hydroxides, which is as a rule effected by adding strong bases such as alkali metal hydroxides or alkaline earth metal hydroxyides, for example sodium hydroxide, potassium hydroxide or calcium hydroxide, or also sodium carbonate. The amount of base is appropriately so chosen that the pH value of the reaction mixture is about 5 to 8. Appropriately, this conversion is carried out in the bath used for application.

At times, the end products show an unpleasant odour caused by volatile, low molecular trivalent phosphorus compounds, for example phosphines, such as trihydroxymethylphosphine. This odour can be eliminated by an oxidative after-treatment of the condensation product, for example by passing air or oxygen into the reaction mixture or by adding oxidising agents such as hydrogen peroxide or potassium persulphate.

The condensation products are used for flameproofing organic fibre material, especially textiles. For this, an appropriate procedure is to apply to these materials an aqueous preparation which contains at least (1) a condensation product of the indicated type and (2) a polyfunctional compound which differs from the condensation products according to (1), and to finish the materials treated in this way by the thermofixing, moist batch, wet batch or ammonia fixing process. The thermofixing process is preferred.

The component (2) is preferably a polyfunctional epoxide or above all a polyfunctional nitrogen compound. Possible epoxides are above all epoxides which are liquid at room temperature and have at least two epoxide groups, which are preferably derived from polyhydric phenols. Polyfunctional nitrogen compounds are, for example, polyalkylenepolyamines or especially compounds which form aminoplasts, or aminoplast precondensates. The latter are preferred.

By compounds which form aminoplasts there are understood nitrogen compounds which can be methylolated and by aminoplast precondensates there are understood addition products of formaldehyde to nitrogen compounds which can be methylolated. As compounds which form aminoplasts or as nitrogen compounds which can be methylolated, there may be mentioned:

1,3,5-aminotriazines such as N-substituted melamines, for example N-butylmelamine, N-trihalogenomethylmelamines, triazones and ammeline, guanamines, for example benzoguanamines and acetoguanamines or also diguanamines.

Further possibilities are: cyanamide, acrylamide, alkylurea or arylurea and alkylthioureas or arylthioureas, alkyleneureas or alkylenediureas, for example, urea, thiourea, urones, ethyleneurea, propyleneurea, acetylenediurea or especially 4,5-dihydroxyimidazolidone-2 and derivatives thereof, for example 4,5-dihydroxyimidazolidone-2 substituted in the 4-position, at the hydroxyl group, by the radical —$CH_2CH_2CO$—NH—$CH_2OH$. The methylol compounds of a urea, of an ethyleneurea or of melamine are preferentially used. Valuable products are in general given by products which are as highly methylolated as possible but in particular also by products with low methylolation. Suitable aminoplast precondensates are both predominantly monomolecular aminoplasts and also more highly precondensed aminoplasts.

The ethers of these aminoplast precondensates can also be used together with the reaction products. For example, the ethers of alkanols such as methanol, ethanol, n-propanol isopropanol, n-butanol or pentanols are advantageous. It is, however, desirable that these aminoplast precondensates should be water-soluble, such as, for example, pentamethylolmelaminedimethylether.

The organic fibre materials which are to be provided with a flameproof finish are, for example, wood, paper, furs, hides or preferably textiles. In particular, fibre materials of polyamides, cellulose, cellulose-polyester or polyester are flameproofed, preferred fabrics being those of wool or polyester, or mixed fabrics of polyester-cellulose, wherein the ratio of the polyester constituent to the cellulose constituent is 1:4 to 2:1. It is thus possible to use, for example, so-called 20/80, 26/74, 50/50 or 67/33 polyester and cellulose mixed fabrics.

The cellulose or cellulose constituent of the fibre material originates, for example, from linen, cotton, rayon or staple viscose. In addition to polyester-cellulose fibre mixtures it is also possible to use fibre mixtures of cellulose with natural or synthetic polyamides. Fibre materials of wool, above all, can also be flameproofed effectively with the polycondensation products.

The aqueous preparations for flameproofing the organic fibre materials as a rule contain 200 to 600 g/l, preferably 350 to 450 g/l, of the component (1) and 20 to 200 g/l, preferably 40 to 120 g/l, of the component (2). The preparations in most cases have an acid to neutral or weakly alkaline pH value.

The preparations for flameproofing can optionally contain yet further additives. To achieve a greater deposit of substance on fabrics it is advantageous, for example, to add 0.1 to 0.5‰ of a high molecular polyethylene glycol. Furthermore, the customary plasticisers can be added to the preparations, for example an aqueous polyethylene emulsion or silicone oil emulsion.

To improve the mechanical strengths of the fibres it is also possible to add to the preparations suitable copolymers, for example copolymers of N-methylolacrylamide or cationic copolymers. Advantageous compositions for this purpose are, for example, aqueous emulsions of copolymers of (a) 0.25 to 10% of an alkaline earth metal salt of an $\alpha,\beta$-ethylenically unsaturated monocarboxylic acid, (b) 0.25 to 30% of a N-methylolamide or N-methylolamide-ether of an $\alpha,\beta$-ethylenically unsaturated monocarboxylic or dicarboxylic acid and (c) 99.5 to 60% of at least one other copolymerisable compound. These copolymers and their manufacture are known. The tear strength and abrasion resistance of the treated fibre material can be favourably influenced by the conjoint use of such a copolymer.

If a polymer of the indicated type is also added to the preparation, it is advantageously added in small amounts, for example 1 to 10% relative to the amount of the condensation product. The same is true of any plasticiser which may be added, where the appropriate amounts can again be 1 to 10%.

It is also possible to add curing catalysts, such as, for example, ammonium chloride, ammonium dihydrogen orthophosphate, phosphoric acid, magnesium chloride or zinc nitrate, but is in most cases not necessary.

The pH value of the preparations is as a rule 2 to 7.5, preferably 4 to 7, and is adjusted in the usual manner by adding base or acid.

It can also be advantageous to add buffer substances, for example $NaHCO_3$, disodium and trisodium phosphate or triethanolamine.

To improve the durability of the flameproof finishes and to achieve a soft handle it can be advantageous to add, to the aqueous preparations, halogenated paraffins in combination with a polyvinyl halide compound.

The preparations are now applied to the fibre materials, which can be done in a manner which is in itself known. Preferably, piece goods are used, and are impregnated on a padder which is fed with the preparation at room temperature.

In the preferred thermofixing process, the fibre material impregnated in this way must now be dried and subjected to a heat treatment. Drying is appropriately carried out at temperatures of up to 100° C. Thereafter the material is subjected to a heat treatment at temperatures above 100° C, for example 100° to 200° C, preferably 120° to 180° C, the duration of which can be the shorter the higher is the temperature. This duration of heating is, for example, 30 seconds to 10 minutes.

If the moist fixing process is used, the fabric is first dried to a residual moisture of about 5 to 20% and is thereafter stored for 12 to 48 hours at about 40° to 60° C, rinsed; washed and dried. In the wet fixing process a similar procedure is followed, except that the completely wet fibre material is stored. In the ammonia fixing process, the treated fibre material is first gas-treated whilst moist and is subsequently dried.

A rinse with an acid-binding agent, preferably with aqueous sodium carbonate solution, can be appropriate in the case of a strongly acid reaction medium.

In the examples which follow, the percentages and parts are percentages by weight and parts by weight, respectively. The relationship of parts by volume to parts by weight is as of ml to g.

EXAMPLE 1

244 parts of a 78% strength aqueous THPC solution (1 mol of THPC), 10.5 parts of cyanamide (0.25 mol) and 200 parts of a xylene isomer mixture are heated to the boil, with rapid stirring, in a stirred vessel of 500 parts by volume capacity which is equipped with a water separator and thermometer. The azeotropic removal of the water from the aqueous THPC solution starts at a boiling point of 102° C. After removal of this water (53.5 parts) the boiling point of the xylene is 130° C. A further 22 parts of water are now removed azeotropically by additional treatment at 130° C, after which the condensation product forms a highly viscous mass. This is cooled to 90° C, the product is dissolved by adding 200 parts of water and the xylene is largely siphoned off. The aqueous solution is completely evaporated in vacuo at 70° C. 168 parts of a highly viscous, colourless condensation product, which gives a copious precipitate with ammonia in aqueous solution, are obtained.

The analysis shows a P-content of 17.2% and a N-content of 3.7%.

The infrared spectrum of this product shows the following bands:

| | |
|---|---|
| Broad | band at approx. 3,200 $cm^{-1}$ strong |
| Sharp | band at approx. 2,910 $cm^{-1}$ weak |

-continued

| | | |
|---|---|---|
| Broad shoulder | band at approx. 2,850 cm$^{-1}$ | medium-strong |
| Broad shoulder | band at approx. 2,620 cm$^{-1}$ | medium |
| Broad shoulder | band at approx. 2,350 cm$^{-1}$ | weak |
| Sharp | band at approx. 2,170 cm$^{-1}$ | weak |
| Sharp | band at approx. 2,070 cm$^{-1}$ | weak |
| Broad | band at approx. 1,640 cm$^{-1}$ | medium |
| Broad | band at approx. 1,540 cm$^{-1}$ | medium |
| Broad | band at approx. 1,410 cm$^{-1}$ | medium |
| Sharp | band at approx. 1,300 cm$^{-1}$ | medium |
| Broad | band at approx. 1,260 cm$^{-1}$ | weak |
| Broad | band at approx. 1,160 cm$^{-1}$ | medium |
| Sharp | band at approx. 1,100 cm$^{-1}$ | weak |
| Sharp | band at approx. 1,040 cm$^{-1}$ | strong |
| Broad | band at approx. 920 cm$^{-1}$ | medium-strong |

EXAMPLE 2

244 parts of a 78% strength aqueous solution of THPC (1 mol of THPC) and 10.5 parts of cyanamide (0.25 mol) are treated for 2 hours at 100° to 105° C internal temperature in a stirred vessel of 500 parts by volume capacity which is equipped with a thermometer and reflux condenser. At the beginning of the treatment, the temperature transiently rises to 110° C. After completion of the treatment, the water is removed in vacuo at 70° C.

199 parts of a colourless, clear precondensate of low viscosity are obtained.

The analysis shows a P-content of 15.3% and a N-content of 3.4%.

The infrared spectrum of this product shows the following bands:

| | | |
|---|---|---|
| Broad | band at approx. 3,200 cm$^{-1}$ | strong |
| Sharp | band at approx. 2,920 cm$^{-1}$ | weak |
| Broad shoulder | band at approx. 2,850 cm$^{-1}$ | medium-strong |
| Broad | band at approx. 2,620 cm$^{-1}$ | medium |
| Broad shoulder | band at approx. 2,350 cm$^{-1}$ | weak |
| Sharp | band at approx. 2,070 cm$^{-1}$ | weak-medium |
| Broad | band at approx. 1,640 cm$^{-1}$ | medium |
| Broad | band at approx. 1,550 cm$^{-1}$ | medium |
| Broad | band at approx. 1,410 cm$^{-1}$ | medium |
| Sharp | band at approx. 1,295 cm$^{-1}$ | weak |
| Sharp | band at approx. 1,260 cm$^{-1}$ | weak |
| Broad | band at approx. 1,190 cm$^{-1}$ | weak |
| Sharp | band at approx. 1,040 cm$^{-1}$ | strong |
| Broad | band at approx. 920 cm$^{-1}$ | medium |

EXAMPLE 3

The procedure described in Example 2 is followed, but 21 parts of cyanamide (0.5 mol) are used.

185 parts of a yellowish, viscous precondensate are obtained.

To facilitate handling on further use, the product is again diluted with water to 70% active substance content.

The infrared spectrum of this product shows the following bands:

| | | |
|---|---|---|
| Broad | band at approx. 3,200 cm$^{-1}$ | strong |
| Sharp | band at approx. 2,920 cm$^{-1}$ | weak |
| Broad shoulder | band at approx. 2,850 cm$^{-1}$ | medium-strong |
| Broad shoulder | band at approx. 2,630 cm$^{-1}$ | medium |
| Broad shoulder | band at approx. 2,350 cm$^{-1}$ | weak |
| Sharp | band at approx. 2,070 cm$^{-1}$ | weak |
| Broad | band at approx. 1,640 cm$^{-1}$ | medium |
| Broad | band at approx. 1,550 cm$^{-1}$ | medium |
| Broad | band at approx. 1,400 cm$^{-1}$ | medium |
| Broad shoulder | band at approx. 1,290 cm$^{-1}$ | medium |
| Sharp | band at approx. 1,260 cm$^{-1}$ | weak |
| Broad | band at approx. 1,190 cm$^{-1}$ | medium-weak |
| Sharp | band at approx. 1,040 cm$^{-1}$ | strong |
| Broad | band at approx. 890 cm$^{-1}$ | medium |

EXAMPLE 4

The procedure described in Example 2 is followed, but additionally 21 parts of 37% strength aqueous formaldehyde solution (0.25 mol) are weighed in.

After completion of the reaction, the mixture is cooled to room temperature. The reaction product is a clear, colourless solution which contains 74% of active substance.

The infrared spectrum of this product shows the following bands:

| | | |
|---|---|---|
| Broad | band at approx. 3,200 cm$^{-1}$ | strong |
| Sharp | band at approx. 2,920 cm$^{-1}$ | weak |
| Broad shoulder | band at approx. 2,850 cm$^{-1}$ | medium |
| Broad shoulder | band at approx. 2,620 cm$^{-1}$ | medium |
| Broad shoulder | band at approx. 2,350 cm$^{-1}$ | weak |
| Sharp | band at approx. 2,070 cm$^{-1}$ | weak |
| Broad | band at approx. 1,640 cm$^{-1}$ | medium |
| Broad | band at approx. 1,540 cm$^{-1}$ | medium |
| Broad | band at approx. 1,410 cm$^{-1}$ | medium |
| Sharp | band at approx. 1,295 cm$^{-1}$ | weak |
| Sharp | band at approx. 1,260 cm$^{-1}$ | weak |
| Broad | band at approx. 1,190 cm$^{-1}$ | weak |
| Broad shoulder | band at approx. 1,100 cm$^{-1}$ | weak |
| Sharp | band at approx. 1,040 cm$^{-1}$ | strong |
| Broad | band at approx. 890 cm$^{-1}$ | medium |

EXAMPLE 5

244 parts of a 78% strength aqueous solution of THPC (1 mol) are neutralised to a pH value of 7.2 by means of 55.6 parts of 30% strength sodium hydroxide solution in a stirred vessel of 500 parts by volume capacity, which is equipped with a thermometer and reflux condenser, and 21 parts of cyanamide (0.5 mol) are subsequently added. Thereafter the mixture is condensed for 2 hours at 100° to 110° C internal temperature. After cooling, a yellow, clear precondensate of low viscosity is obtained, which contains 63% of active substance.

The infrared spectrum of this product shows the following bands:

| | | |
|---|---|---|
| Broad | band at approx. 3,240 cm$^{-1}$ | strong |
| Broad | band at approx. 2,910 cm$^{-1}$ | weak |
| Broad shoulder | band at approx. 2,850 cm$^{-1}$ | medium |
| Broad shoulder | band at approx. 2,640 cm$^{-1}$ | medium |
| Broad shoulder | band at approx. 2,360 cm$^{-1}$ | medium |
| Sharp | band at approx. 2,080 cm$^{-1}$ | medium |
| Broad | band at approx. 1,640 cm$^{-1}$ | medium-strong |
| Broad | band at approx. 1,545 cm$^{-1}$ | medium |
| Broad | band at approx. 1,400 cm$^{-1}$ | medium |
| Sharp | band at approx. 1,300 cm$^{-1}$ | weak-medium |
| Broad | band at approx. 1,130 cm$^{-1}$ | medium |
| Sharp | band at approx. 1,040 cm$^{-1}$ | medium-strong |
| Sharp shoulder | band at approx. 920 cm$^{-1}$ | medium |
| Broad | band at approx. 885 cm$^{-1}$ | weak |

EXAMPLE 6

244 parts of a 78% strength aqueous THPC solution (1 mol), 10.5 parts of cyanamide (0.25 mol) and 200 parts of benzene are heated to the boil, with rapid stirring, in a stirred vessel of 500 parts by volume capacity which is equipped with a water separator and thermometer. A total of 57.5 parts of water are removed azeotropically over the course of 8 hours at a boiling point of 75° to 78° C. Further separation of water is not observed. The reaction product is a very highly viscous mass. The benzene is then largely siphoned off and the resin is dissolved in 200 parts of water. The aqueous solution containing benzene is completely evaporated in vacuo at about 70° C. 194 parts of a viscous condensation product are obtained and are diluted with water to 80% active substance content in order to facilitate handling.

The infrared spectrum of this product shows the following bands:

| | |
|---|---|
| Broad | band at approx. 3,200 cm$^{-1}$ strong |
| Sharp | band at approx. 2,920 cm$^{-1}$ weak |
| Broad shoulder | band at approx. 2,350 cm$^{-1}$ medium |
| Broad shoulder | band at approx. 2,620 cm$^{-1}$ medium |
| Sharp | band at approx. 2,070 cm$^{-1}$ weak |
| Broad | band at approx. 1,640 cm$^{-1}$ medium |
| Broad | band at approx. 1,550 cm$^{-1}$ medium |
| Broad | band at approx. 1,415 cm$^{-1}$ medium |
| Sharp | band at approx. 1,300 cm$^{-1}$ weak |
| Sharp | band at approx. 1,260 cm$^{-1}$ weak |
| Broad | band at approx. 1,190 cm$^{-1}$ weak |
| Sharp | band at approx. 1,040 cm$^{-1}$ strong |
| Sharp shoulder | band at approx. 920 cm$^{-1}$ medium |
| Broad shoulder | band at approx. 880 cm$^{-1}$ medium |

EXAMPLE 7

190.5 parts (1 mol) of crystalline anhydrous THPC and 0.84 part (0.02 mol) of cyanamide are condensed for 2 hours in the melt, at 105° – 110° C internal temperature, in a stirred vessel of 500 parts by volume capacity which is equipped with a reflux condenser and thermometer. After cooling, 190 parts of colourless, waxy condensation product are obtained.

The infrared spectrum of this product shows the following bands:

| | |
|---|---|
| Broad | band at approx. 3,200 cm$^{-1}$ strong |
| Sharp | band at approx. 2,920 cm$^{-1}$ weak |
| Broad shoulder | band at approx. 2,830 cm$^{-1}$ medium |
| Broad shoulder | band at approx. 2,610 cm$^{-1}$ medium |
| Sharp | band at approx. 2,070 cm$^{-1}$ weak |
| Broad | band at approx. 1,630 cm$^{-1}$ medium |
| Broad | band at approx. 1,430 cm$^{-1}$ medium |
| Sharp | band at approx. 1,300 cm$^{-1}$ weak |
| Sharp | band at approx. 1,040 cm$^{-1}$ strong |
| Sharp shoulder | band at approx. 920 cm$^{-1}$ medium |
| Broad shoulder | band at approx. 880 cm$^{-1}$ medium |

EXAMPLE 8

176 parts of a condensate manufactured according to Example 7 are dissolved in the same apparatus in 100 parts of methanol, 0.1 part of 36% strength aqueous hydrochloric acid is added and etherification is carried out for 30 minutes at the reflux temperature (64°–65° C). Thereafter the mixture is cooled to 50° C and the excess methanol is removed in vacuo, whilst stirring, until constant weight is reached.

207 parts of a yellowish product, which partially crystallises, are obtained.

The infrared spectrum of this product shows the following bands:

| | |
|---|---|
| Broad | band at approx. 3,240 cm$^{-1}$ strong |
| Sharp | band at approx. 2,920 cm$^{-1}$ weak |
| Broad shoulder | band at approx. 2,850 cm$^{-1}$ medium |
| Broad | band at approx. 2,620 cm$^{-1}$ medium |
| Broad shoulder | band at approx. 2,470 cm$^{-1}$ weak |
| Broad shoulder | band at approx. 2,350 cm$^{-1}$ weak |
| Sharp | band at approx. 2,070 cm$^{-1}$ weak-medium |
| Broad | band at approx. 1,630 cm$^{-1}$ medium-strong |
| Broad | band at approx. 1,420 cm$^{-1}$ medium-strong |
| Sharp | band at approx. 1,295 cm$^{-1}$ weak |
| Broad | band at approx. 1,195 cm$^{-1}$ weak |
| Sharp | band at approx. 1,040 cm$^{-1}$ medium-strong |
| Sharp shoulder | band at approx. 920 cm$^{-1}$ medium |
| Broad shoulder | band at approx. 880 cm$^{-1}$ weak-medium |

EXAMPLE 9

Fabrics of polyester/cotton, 67:33 (PES/CO), polyester (PES), cotton serge (CO) and wool gabardine (W) are padded with the liquors of the table which follows, dried at 80° to 100° C and subsequently cured for 5 minutes at 150° C (thermofixing process). In addition to the thermofixing process, the ammonia fixing process can also be used. The padded fabric is dried at 80° C (not completely), gassed with ammonia for 5 minutes, then padded in a liquor which contains 300 ml of a 24% strength aqueous ammonia solution per liter, and, after a dwell time of 5 minutes in air, dried at about 80° C.

The wool fabric and the polyester fabric are washed for 5 minutes at 40° C in a liquor which per liter contains 4 g of sodium carbonate and 1 g of a 25% strength aqueous solution of a condensation product of 1 mol of p-tert.-nonylphenol and 9 mols of ethylene oxide. Thereafter the fabric is rinsed and dried.

The polyester-cotton fabric and the cotton fabric are respectively washed for 5 minutes at 60° C or 5 minutes at 95° C with a liquor which per liter contains 5 ml of hydrogen peroxide (35% strength), 3 g of aqueous sodium hydroxide solution (30% strength) and 1 g of a 25% strength aqueous solution of a condensation product of 1 mol of p-tert.-nonylphenol and 9 mols of ethylene oxide. Thereafter the fabric is rinsed and dried.

The fabrics are then washed up to 40 times for 45 minutes and at temperatures of 40° C, 60° C or 95° C in a domestic washing machine, using a liquor which contains 4 g/l of a domestic detergent (SNV 198,861 wash).

The individual fabrics are then tested for their flameproof character (DIN 53,906 vertical test; ignition time 6 seconds). Untreated fabrics burn away.

For pure polyester fabric, the test of the flameproof character is carried out in accordance with the AATCC Test Method 34-1969. The degree of fixing indicates the amount of the flameproofing agent after rinsing, as a percentage of the original uptake.

The results are summarised in Table 2 below.

Table 1

| | Treated with liquor | | | | | | |
|---|---|---|---|---|---|---|---|
| | A | | | | B | | |
| | Thermofixing process | | | | Ammonia fixing process | | |
| Constituents | PES/CO | PES | CO | W | PES/CO | CO | W |
| Product according to | 440 | 430 | 189 | 325 | 440 | 250 | 325 |

Table 1-continued

| | Treated with liquor | | | | | | |
|---|---|---|---|---|---|---|---|
| | A | | | | B | | |
| | Thermofixing process | | | | Ammonia fixing process | | |
| Constituents | PES/CO | PES | CO | W | PES/CO | CO | W |
| Example 1, g/l | | | | | | | |
| Dimethylolmelamine, g/l | 103 | 120 | 96 | 70 | — | — | — |
| Condensation+) product g/l | — | — | — | 2 | 2 | 2 | 2 |
| pH value of the liquor (adjusted with NaOH) | 5.5 | 5.5 | 5.5 | 5.5 | 5.5 | 5.5 | 5.5 |
| Liquor uptake, % | 73 | 80 | 80 | 66 | 73 | 77 | 68 |
| Degree of fixing, % | 75 | 81 | 81 | 68 | 88 | 55 | 69 |

+)Condensation product of p-tert.-nonylphenol + 9 mols of ethylene oxide

| | Smouldering time [seconds]/Tear length [cm] | | | | | | |
|---|---|---|---|---|---|---|---|
| | Thermofixing process | | | | Ammonia fixing process | | |
| Flameproof characters | PES/CO | PES | CO | W | PES | CO | W |
| After rinsing | 0/12 | 3/13.5 | 0/7 | 0/4 | 0/11.5 | 0/4.5 | 0/2 |
| After 5 washes (40° C) | — | — | — | 0/3 | — | — | 0/1.5 |
| After 10 washes (40° C) | — | — | — | 9/7 | — | — | 6/6 |
| After 20 washes (60° C) | 0/10.5 | — | 0/8 | — | 0/11.5 | 0/5 | — |
| After 40 washes (60° C) | 0/8.5 | — | 0/7 | — | 0/10 | 0/5 | — |

Table 2

| | Treated with liquor | | | | | | | | | |
|---|---|---|---|---|---|---|---|---|---|---|
| | B | | | C | | D | | E | | F |
| Constituents (g/l) | PES/CO | PES | CO | PES/CO | PES | PES/CO | PES | PES/CO | PES | PES/CO |
| Product according to Example 2 | 440 | 432 | 189 | — | — | — | — | — | — | — |
| Product according to Example 3 | — | — | — | 650 | 685 | — | — | — | — | — |
| Product according to Example 4 | — | — | — | — | — | 745 | 780 | — | — | — |
| Product according to Example 5 | — | — | — | — | — | — | — | 655 | 850 | — |
| Product according to Example 6 | — | — | — | — | — | — | — | — | — | 485 |
| Dimethylolmelamine | 103 | 120 | 96.5 | 96.5 | 120 | 96.5 | 120 | 72.5 | 120 | 96.5 |
| Condensation product+) | — | — | — | — | 0.5 | — | — | — | — | — |
| Silicone oil emulsion (40% strength) | 30 | — | — | — | — | — | — | — | — | — |
| pH value of the liquor (adjusted with NaOH) | 5.5 | 5.5 | 5.5 | 5.9 | 5.6 | 5.5 | 5.5 | 5.5 | 5.5 | 5.5 |
| Liquor uptake (%) | 70 | 90 | 80 | 75 | 80 | 75 | 75 | 70 | 70 | 75 |
| Degree of fixing (%) | 69 | 75 | 84 | 75 | 78 | 66 | 73 | 68 | 60 | 73 |

+)See Table 1

| | Smouldering time [seconds]/Tear length [cm] | | | | | | | | | |
|---|---|---|---|---|---|---|---|---|---|---|
| | B | | | C | | D | | E | | F |
| Flameproof character | PES/CO | PES | CO | PES/CO | PES | PES/CO | PES | PES/CO | PES | PES/CO |
| After rinsing | 0/11 | 13/12.5 | 0.75 | 0/9.5 | 3/12.5 | 0/14 | — | 0/11 | 6/14.5 | 0/10.5 |
| After 20 washes (60° C) | 0/9.5 | — | — | 0/9.5 | — | 0/11 | — | 0/10 | — | 0/8.5 |
| After 40 washes (60°) | 0/9.5 | — | — | 0/9.5 | — | 0/11 | — | — | — | 0/10 |

EXAMPLE 10

Fabrics of polyester/cotton (PES/CO), 67:33 and 50:50, are padded with the liquors of Table 3 below, and then aftertreated as follows:

a. By the thermofixing process, as indicated in Example 9, with subsequent washing at 60° C as indicated in Example 9.

b. Partly by the moist fixing process or moist batch process: after padding, batch at 10% residual moisture content for 24 hours at up to 50° C, subsequently rinse with cold water, wash for 5 minutes in a bath which contains 4 g/l of sodium carbonate and 1 g/l of a condensation product of 1 mol of p-tert.-nonylphenol and 9 mols of ethylene oxide, then rinse and dry.

c. Partly by the wet fixing or wet batch process: after padding, batch wet for 24 hours at 50° C and subsequently rinse and wash as under (b).

The fabrics are then washed up to 20 times at 60° C as indicated in Example 9 and are thereafter tested for their flameproof character according to DIN 53,906 (ignition time 6 seconds). Untreated fabrics burn away.

The results are summarised in Table 3 which follows.

Table 3

| Constituents | Treated with | | | | | | |
|---|---|---|---|---|---|---|---|
| | PES/CO 50:50 | | | | PES/CO 67:31 | | |
| | I | II | III | III | I | II | III |
| g/l | T | T | M | W | T | T | M |
| Product according to Example 8 | 545 | — | — | — | 545 | — | — |
| Product according to Example 3 | — | 530 | 530 | 530 | — | 530 | 530 |
| Di-Trimethylolmelamine | 103 | — | 103 | 103 | 103 | — | 103 |
| Trimethylolmelamine-dimethyl-ether (75% strength) | — | 153 | — | — | — | 153 | — |
| Silicone oil emulsion (40% strength) | 35 | 35 | 35 | 35 | 35 | 35 | 35 |
| pH value of the liquor | 5.5 | 7 | 4.5 | 4.5 | 5.5 | 7 | 4.5 |
| Liquor uptake, % | 70 | 70 | 70 | 10 | 70 | 70 | 20 |
| g of phosphorus/kg of fabric | 57 | 57 | 57 | 57 | 57 | 57 | 57 |
| g of nitrogen/kg of fabric | 30 | 30 | 30 | 30 | 30 | 30 | 30 |

| | Flameproof character: smouldering time (seconds) /Tear length (cm) | | | | | | |
|---|---|---|---|---|---|---|---|
| After rinsing | 0/7.5 | 0/7.5 | 0/7.5 | 0/8.5 | 0/9.5 | 0/10 | 0/10 |
| After 1 wash | 0/7 | 0/5 | 0/4 | 0/7 | 0/9 | 0/8 | 0/7 |
| After 5 washes | 0/5 | 0/7 | 0/7 | 0/6 | 0/7 | 0/8 | 0/7 |
| After 20 washes | 0/13 | 0/7 | 0/8 | 0/9 | 0/9 | 0/8 | 0/8 |

T: Thermofixing process (a)
M: Moist batch process (b)
W: Wet batch process (c)

We claim:

1. A water-soluble condensation product from tetrakis-(hydroxymethyl)-phosphonium compound and cyanamide, produced by the process, comprising condensing a tetrakis-(hydroxymethyl)-phosphonium salt or tetrakis-(hydroxymethyl)-phosphonium hydroxide with cyanamide, at a molar ratio of 1:0.02 to 0.5, at 40° to 120° C. in the presence of an inert organic solvent or aqueous medium or in the melt, to give the condensation product, while simultaneously removing by distillation from the reaction mixture any water present or formed during the condensation.

2. A product of claim 1, wherein the condensation is carried out in the presence of an inert organic solvent.

3. A product of claim 1, wherein the inert organic solvent is an aromatic hydrocarbon.

4. A product of claim 1, wherein reaction mixture further includes formaldehyde or paraformaldehyde.

5. A product of claim 1, wherein further condensation occurs as the reaction temperature is elevated to 100° to 150° C after removal of the water.

6. A product of claim 1, wherein the resulting condensation product is further treated with an alkanol of 1 to 4 carbon atoms in an acid medium to effect partial or complete etherification.

7. A product of claim 1, wherein the molar ratio is 1:0.1 to 1:0.3.

8. A product of claim 1, wherein the tetrakis-(hydroxymethyl)-phosphonium salt is a tetrakis-(hydroxymethyl)-phosphonium halide.

9. A product of claim 8, wherein the tetrakis-(hydroxymethyl)-phosphonium halide is tetrakis-(hydroxymethyl)-phosphonium chloride.

* * * * *